United States Patent
Nuggehalli et al.

(10) Patent No.: US 9,275,349 B2
(45) Date of Patent: *Mar. 1, 2016

(54) HEALTHCARE SYSTEM INTEGRATION

(71) Applicants: Jayasimha Nuggehalli, Cupertino, CA (US); Zhenyu Lu, Cupertino, CA (US)

(72) Inventors: Jayasimha Nuggehalli, Cupertino, CA (US); Zhenyu Lu, Cupertino, CA (US)

(73) Assignee: Ricoh Company Ltd., Tokyo (JP)

( * ) Notice: Subject to any disclaimer, the term of this patent is extended or adjusted under 35 U.S.C. 154(b) by 176 days.

This patent is subject to a terminal disclaimer.

(21) Appl. No.: 13/946,650

(22) Filed: Jul. 19, 2013

(65) Prior Publication Data
US 2015/0026175 A1  Jan. 22, 2015

(51) Int. Cl.
*G06F 17/30* (2006.01)
*G06Q 10/00* (2012.01)

(52) U.S. Cl.
CPC .......... *G06Q 10/00* (2013.01); *G06F 17/30038* (2013.01)

(58) Field of Classification Search
CPC ....... G06Q 40/08; G06Q 50/22; G06Q 10/00; G06F 19/328; G06F 19/322; G06F 19/3431; G06F 17/30038; G06F 17/30; G06F 19/3425; G06F 19/3406; G06F 19/3418; G06F 19/3487; H04B 1/385; H04B 2001/3866
USPC .......... 707/758, 736, 769, E17.005, E17.014, 707/E17.017, E17.041, E17.044, E17.108; 705/2, 3, 4; 600/27, 301, 306
See application file for complete search history.

(56) References Cited

U.S. PATENT DOCUMENTS

| | | |
|---|---|---|
| 5,850,254 A | 12/1998 | Takano et al. |
| 6,067,111 A | 5/2000 | Hahn et al. |
| 6,246,933 B1 | 6/2001 | Bague |
| 7,978,219 B1 | 7/2011 | Imes |
| 7,991,646 B2 | 8/2011 | Lewis et al. |
| 8,589,239 B2 | 11/2013 | Zacarias et al. |
| 2002/0009978 A1 | 1/2002 | Dukach et al. |
| 2002/0194226 A1 | 12/2002 | Sheth et al. |
| 2002/0194502 A1 | 12/2002 | Sheth et al. |
| 2003/0212567 A1 | 11/2003 | Shintani et al. |
| 2005/0131738 A1 | 6/2005 | Morris |
| 2005/0135738 A1* | 6/2005 | Shin et al. ......................... 385/27 |
| 2007/0203748 A1* | 8/2007 | Rothpearl et al. ................ 705/2 |
| 2008/0042825 A1 | 2/2008 | Denny et al. |
| 2008/0091465 A1* | 4/2008 | Fuschino et al. ................. 705/2 |

(Continued)

OTHER PUBLICATIONS

William D. Eggers and Joshua Jaffe—"Gov on the Go Boosting public sector productivity by going mobile" 2013—pp. 1-32.*

(Continued)

*Primary Examiner* — Anh Ly
(74) *Attorney, Agent, or Firm* — Hickman Palermo Becker Bingham LLP; Edward A. Becker

(57) ABSTRACT

An approach is provided for acquiring and integrating data into external services. According to the approach, image and/or video data and identification data are received from a client device. The image and/or video data includes one or more images and/or video data of an object that are acquired by the client device and the identification data is data that uniquely identifies the object. Record data is generated and stored that includes the identification data and at least a reference to the image and/or video data. The image and/or video data and the identification data are transmitted to an external service. This identification data allows an external service to associate the image and/or video data with other data maintained by the external service.

20 Claims, 16 Drawing Sheets

(56) References Cited

U.S. PATENT DOCUMENTS

| | | | |
|---|---|---|---|
| 2008/0167106 A1* | 7/2008 | Lutnick | G07F 17/32 463/16 |
| 2008/0174676 A1* | 7/2008 | Squilla | G06F 17/30056 348/231.6 |
| 2008/0255887 A1 | 10/2008 | Gruter | |
| 2009/0030366 A1* | 1/2009 | Hochman | 604/67 |
| 2009/0106127 A1 | 4/2009 | Purdy et al. | |
| 2009/0138290 A1 | 5/2009 | Holden | |
| 2009/0140887 A1 | 6/2009 | Breed et al. | |
| 2009/0254971 A1 | 10/2009 | Herz et al. | |
| 2009/0295626 A1 | 12/2009 | Su | |
| 2009/0299767 A1* | 12/2009 | Michon et al. | 705/3 |
| 2010/0148937 A1 | 6/2010 | Howard | |
| 2010/0211431 A1* | 8/2010 | Lutnick | G06Q 30/02 705/14.12 |
| 2011/0125527 A1* | 5/2011 | Nair | 705/3 |
| 2011/0125528 A1* | 5/2011 | Padate et al. | 705/3 |
| 2011/0301441 A1* | 12/2011 | Bandic et al. | 600/306 |
| 2012/0105197 A1 | 5/2012 | Kobres | |
| 2012/0120220 A1* | 5/2012 | Al-Moosawi | 348/77 |
| 2012/0173900 A1* | 7/2012 | Diab | H04L 12/10 713/310 |
| 2012/0321759 A1* | 12/2012 | Marinkovich et al. | 426/231 |
| 2013/0154850 A1* | 6/2013 | Chan et al. | 340/870.02 |
| 2013/0154851 A1* | 6/2013 | Gaskill et al. | 340/870.02 |
| 2013/0344859 A1 | 12/2013 | Abramson | |
| 2014/0028447 A1 | 1/2014 | Howard | |
| 2014/0309845 A1 | 10/2014 | Wittmann | |
| 2014/0324247 A1 | 10/2014 | Jun | |
| 2015/0019266 A1* | 1/2015 | Stempora | G06Q 40/08 705/4 |
| 2015/0025917 A1* | 1/2015 | Stempora | G06Q 40/08 705/4 |
| 2015/0026174 A1 | 1/2015 | Nuggehalli et al. | |
| 2015/0170290 A1* | 6/2015 | Bowne | G06Q 10/0639 705/4 |
| 2015/0287130 A1 | 10/2015 | Vercollone | |

OTHER PUBLICATIONS

Emily Rose—"The Effectiveness of Checklists versus Bar-codes Towards Detecting Medication Planning and Execution Errors"—Institute of Biomaterials and Biomedical Engineering University of Toronto © Copyright by Emily Rose 2012: pp. 1-179.*

Ebay iPhone App 2.0—Selling, http://www.youtube.com/watch?v=Pj7ie8g0x9c, published Nov. 17, 2010, last accessed Sep. 3, 2014, 2 pages.

U.S. Appl. No. 13/763,950, filed Feb. 11, 2013, Final Office Action, Feb. 13, 2015.

U.S. Appl. No. 13/946,639, filed Jul. 19, 2013, Office Action, May 14, 2015.

U.S. Appl. No. 13/763,950, filed Feb. 11, 2013, Interview Summary, Jul. 24, 2015.

How to Shop Savvy with Redlaser, Bryan Shields, Mar. 22, 2010, http://iphone.appstorm.net/reviews/lifestyle/how-to-shop-savvy-with-redlaser.

Ebay Buys Redlaser, Hopes Barcode Scanning Encourages Selling, Geoffrey A. Fowler, Jun. 23, 2010, http://blogs.wsj.com/digits/2010/06/23/edbay-buys-redlaser-hopes-barcode-scanning-encourages-selling.

Filipova-Neumann el. al., "Reducing Asymmetric Information in Insurnace Markets: Cars with Black Boxes", Telematics and Informatics dated 2010, 10 Pages.

* cited by examiner

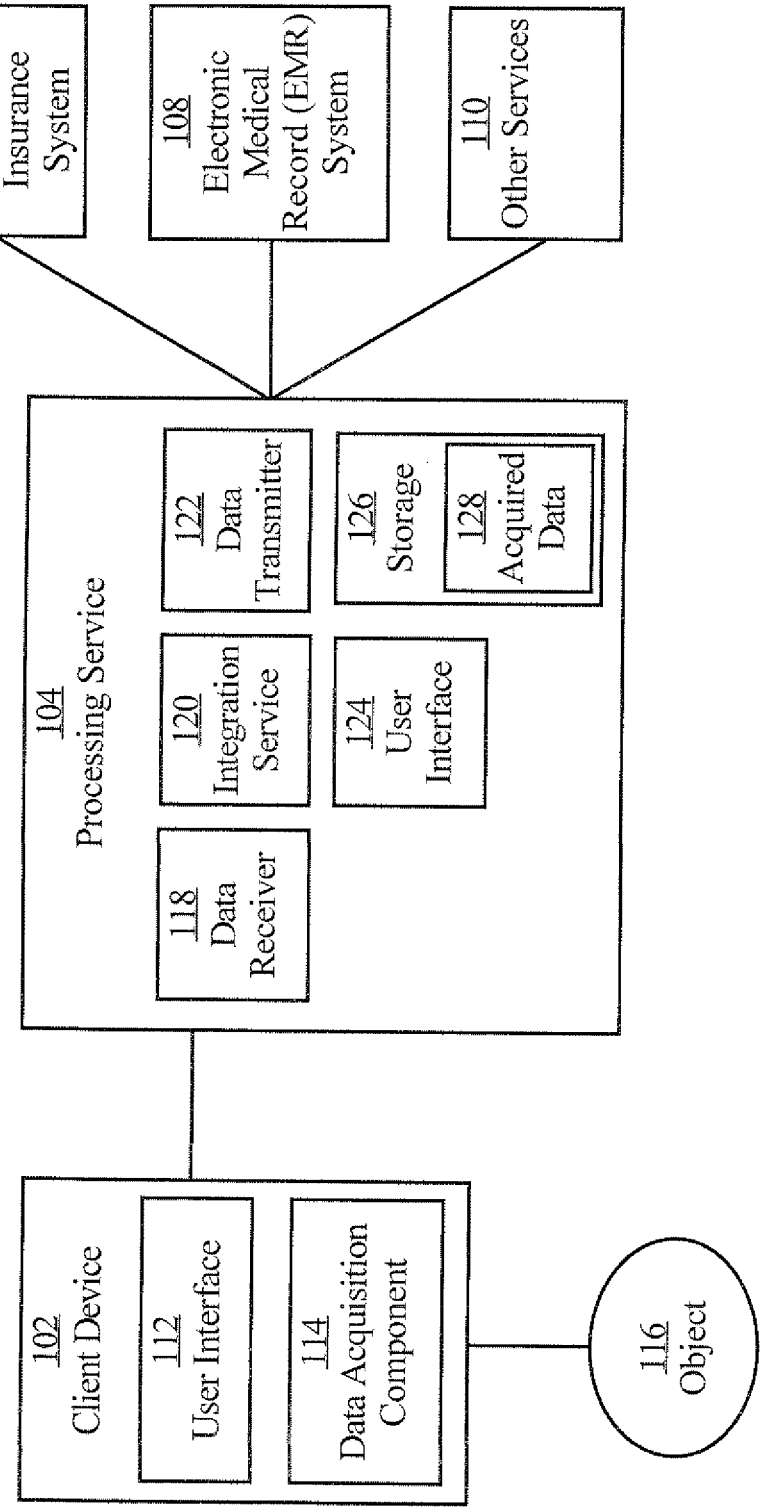

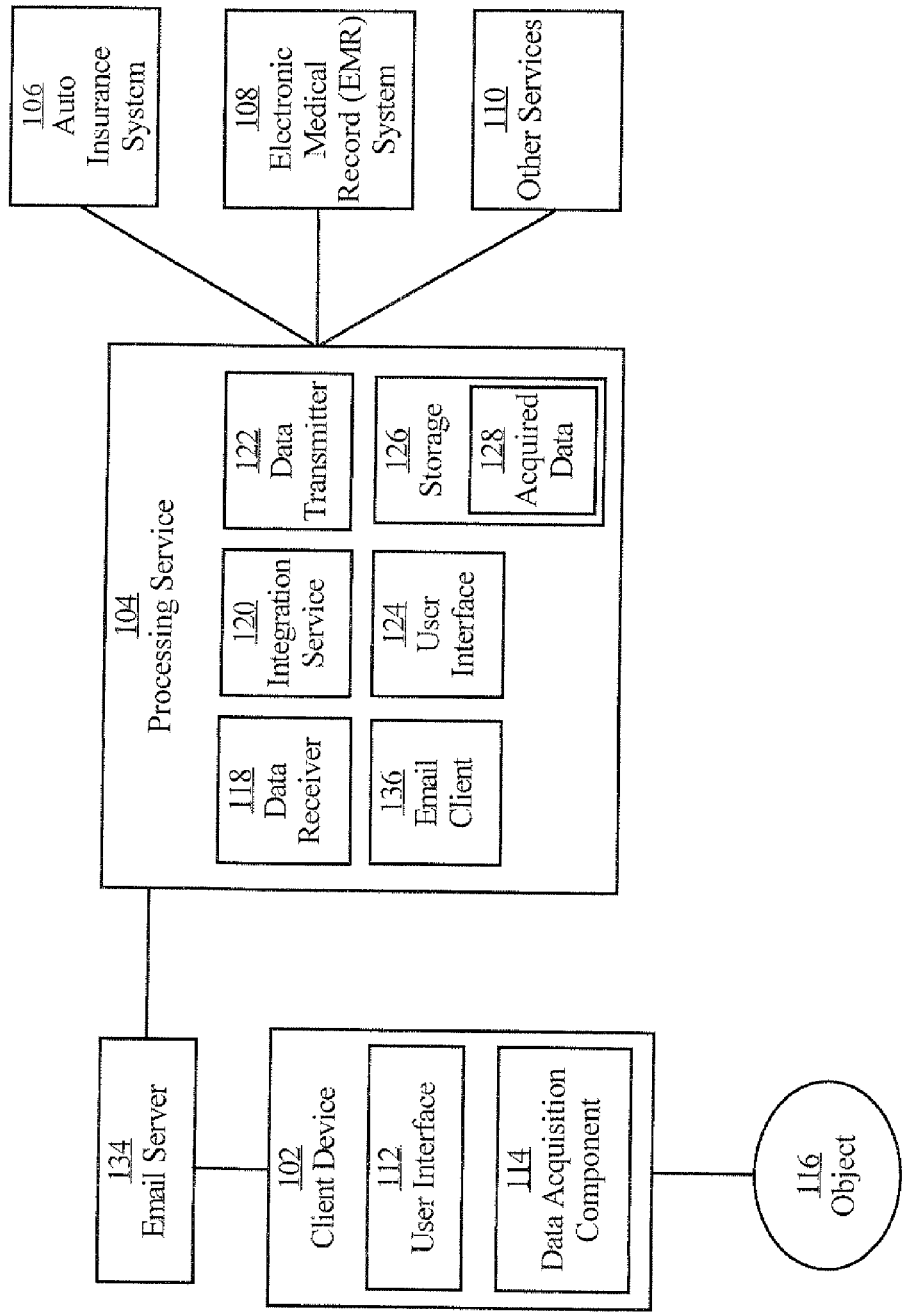

Send Data To Service

350

Select Data 352

| Image Data | Add Memo | Include Loc |
|---|---|---|
| Image 001 | ☒ ☐ ☐ | ☒ ☐ ☐ |
| Image 002 | | |
| Image 003 | | |
| Scan Data | | |
| Scan 001 | | |

Select Service 354

Auto Insurance Service #1
Auto Insurance Service #2
Auto Insurance Service #3

OK    CANCEL

356

FIG. 5A
| Insurance Claim Number | 3522566 |
|---|---|
| Vendor Name | xxyyzz |
| Part Cost | $12.00 |
| POS Barcode | 13389019239 |
FIG. 5B
| Patient ID | 3522566 |
|---|---|
| Doctor ID | 2344566 |
| Comment | Doctor's Comment..... |
FIG. 6A
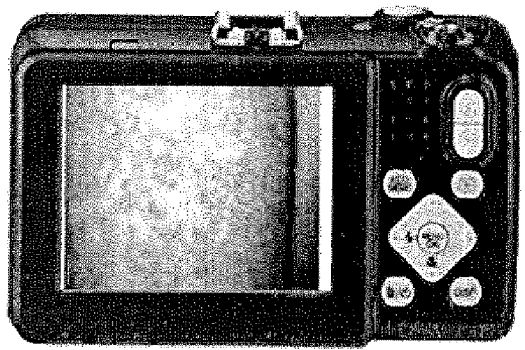
FIG. 6B
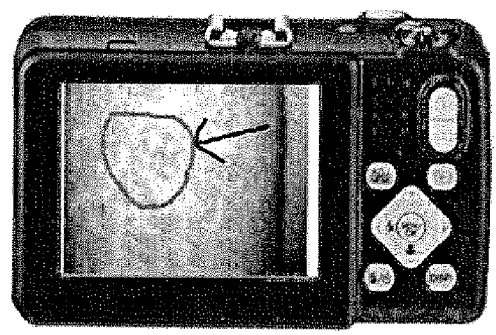

FIG. 8A

| | User Table |
|---|---|
| PK | ID |
| | User ID
Auth Token
FTP Folder
Email Address |

| | Insurance Claim Item |
|---|---|
| PK | ID |
| | User ID
Barcode
Memo
ImageLink
Status
GPS Data |

FIG. 8B

| | User Table |
|---|---|
| PK | ID |
| | User ID
Auth Token
FTP Folder
Email Address |

| | Patient Image Item |
|---|---|
| PK | ID |
| | Patient ID
Memo
ImageLink
GPS Data
Annotation |

HEALTHCARE SYSTEM INTEGRATION

FIELD OF THE INVENTION

Embodiments relate generally to acquiring and integrating data into external services, and more specifically, to streamlining the process of acquiring and integrating data into external services.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

An increasing number of mobile devices, such as smartphones and tablet computers, are equipped with cameras. This makes them increasingly valuable to individuals and businesses. One of the issues with mobile devices that include cameras is that it can be difficult for business users to upload acquired images to external services, such as business applications. Users typically do not have the specialized knowledge or skills to access the interfaces provided by external services and therefore must rely upon dedicated applications executing on their mobile devices to be able to upload images from their mobile devices to external services. Even with such dedicated applications, it can be difficult for users to associate images with particular data records managed by the external services.

SUMMARY

An approach is provided for integrating data into an electronic medical record system. Both first image data associated with a first patient and first identification data that uniquely identifies the first patient are received from a first client device having at least a data acquisition component. First record data is generated and stored that includes the first identification data and at least a reference to the first image data. Both second image data associated with a second patient and second identification data that uniquely identifies the second patient are received from a second client device having at least a data acquisition component. Second record data is generated and stored that includes the second identification data and at least a reference to the second image data. The first image data associated with the first patient, the first identification data that uniquely identifies the first patient, the second image data associated with the second patient and the second identification data that uniquely identifies the second patient are transmitted to an electronic medical record system that is external to the apparatus.

BRIEF DESCRIPTION OF THE DRAWINGS

In the figures of the accompanying drawings like reference numerals refer to similar elements.

FIGS. 1A-1E are block diagrams that depict arrangements for acquiring and integrating data into external services.

FIG. 3B depicts an example graphical user interface that allows a user to select image data and scan data acquired at the site of an automobile accident and transfer the selected image data and scan data to an auto insurance service.

FIG. 5A depicts a table of example memo information that may be entered by a user for an automobile involved in an accident.

FIG. 5B depicts a table of example memo information that may be entered by a user for a patient in the electronic medical record (EMR) context.

FIGS. 6A and 6B depicts a graphical user interface of a client device in the form of a camera that displays a region on a patient's body.

FIG. 8A depicts an example data structure implemented by a processing service in the auto insurance context.

FIG. 8B depicts an example data structure implemented by a processing service in the EMR context.

FIGS. 12A and 12B depict example administrative user interface screens in the EMR context.

DETAILED DESCRIPTION

Figure 1B:
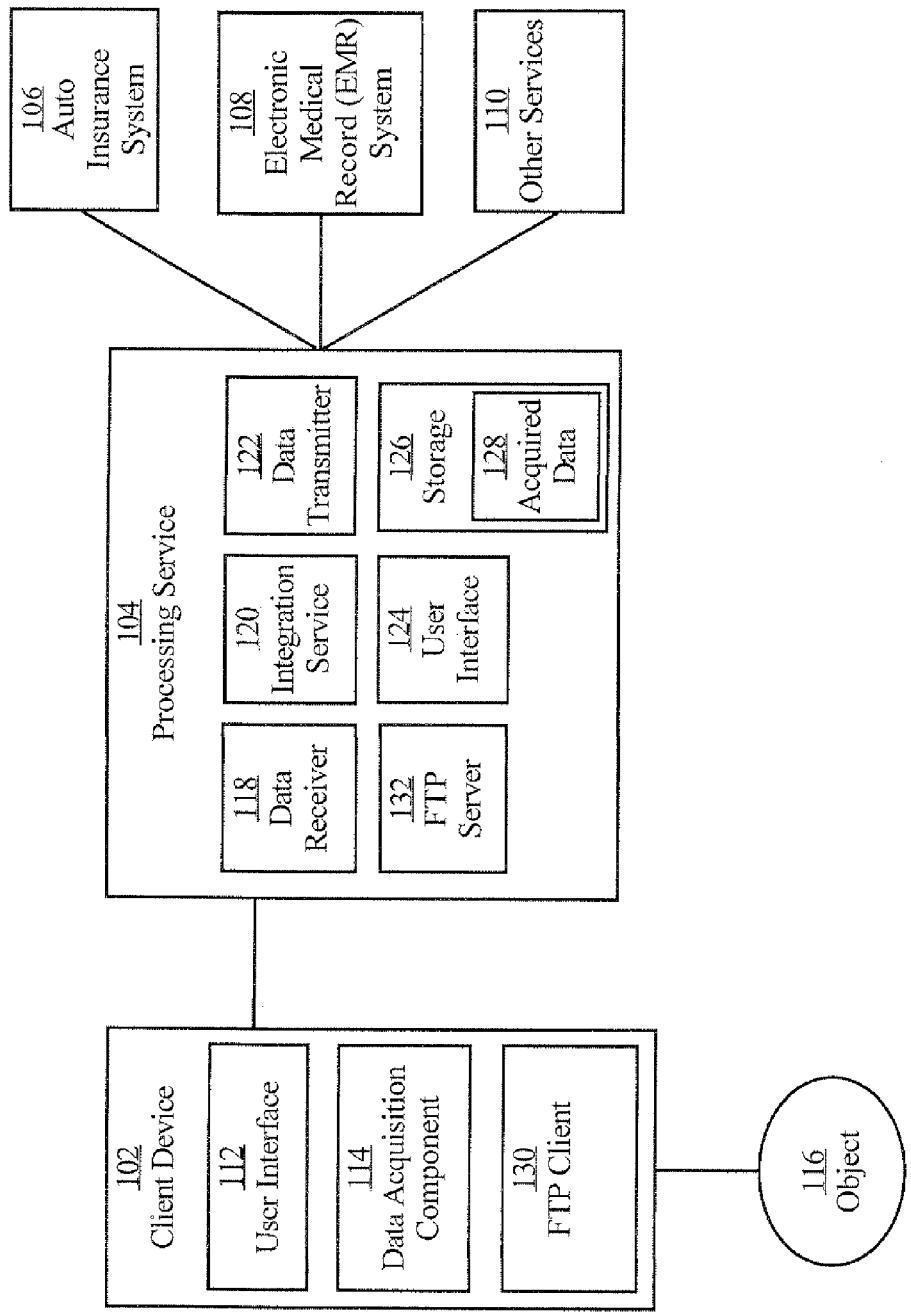

In the following description, for the purposes of explanation, numerous specific details are set forth in order to provide a thorough understanding of the embodiments. It will be apparent, however, to one skilled in the art that the embodiments may be practiced without these specific details. In other instances, well-known structures and devices are shown in block diagram form in order to avoid unnecessarily obscuring the embodiments.

I. OVERVIEW
II. SYSTEM ARCHITECTURE
  A. Client Device
  B. Processing Service
III. CLIENT DEVICE CONFIGURATION AND DATA ACQUISITION
IV. DATA RECEPTION AND PROCESSING
V. TRANSFERRING ACQUIRED DATA TO EXTERNAL SERVICES
VI. PROCESSING SERVICE ADMINISTRATION
VII. IMPLEMENTATION MECHANISMS I. Overview An approach is provided for acquiring and integrating data into external services. According to the approach, image and/or video data and identification data are received from a client device. The image and/or video data includes one or more images and/or video data of an object that are acquired by the client device and the identification data is data that uniquely identifies the object. Record data is generated and stored that includes the identification data and at least a reference to the image and/or video data. The image and/or video data and the identification data are transmitted to an external service. This identification data allows an external service to associate the image and/or video data with other data maintained by the external service.

The approach is beneficial in a wide variety of contexts in which it helpful for a user to upload acquired data to external services and have the acquired data automatically associated with other data maintained by the external services. For example, the approach may be useful in the auto insurance industry to allow a user to use a client device, such as a camera, smartphone, tablet computer, etc., to acquire image and/or video data of an automobile involved in an accident, upload the image and/or video data to an auto insurance system and have the image and/or video data be automatically associated with insurance claim records maintained by the auto insurance system. As another example, the approach may be useful in the electronic medical record industry to allow a user to use a client device to acquire image and/or video data of a patient, upload the image and/or video data to an electronic medical record system and have the image and/or video data automatically associated with records for the patient maintained by the electronic medical record system. In both examples, the user does not need to have specific knowledge of the interfaces or other mechanisms used to upload the acquired data to the auto insurance system or the electronic medical record system. The approach is applicable to integrating into external services data acquired by multiple client devices.

II. System Architecture

FIG. 1A is a block diagram that depicts an arrangement 100 for acquiring and integrating data into external services. Arrangement 100 includes a client device 102, a processing service 104, an auto insurance system 106, an electronic medical record (EMR) system 108 and other services 110. Arrangement 100 is not limited the particular elements depicted in FIG. 1A and may include fewer or additional elements depending upon a particular implementation. Embodiments are described herein in the context of a single client device 102 for purposes of explanation, but the approach is applicable to any number of client devices. The various elements depicted in FIG. 1A are communicatively coupled via one or more communications links that may include, for example, any number and type of wired or wireless networks, such as local area networks (LANs), wide area networks (WANs), the Internet, etc., as well as direct communications links.

A. Client Device

Client device 102 is configured to perform data acquisition and transmit the acquired data to other devices. According to one embodiment, client device 102 is configured to acquire image and/or video data of object 116 and identification data that uniquely identifies object 116 and transmit the acquired image and/or video data and identification data to other devices. For example, in the context of object 116 being an automobile, client device 102 may acquire image and/or video data of the automobile and identification data that uniquely identifies the automobile and transmit the image and/or video data and identification data to processing service 104. As another example, in the context of object 116 being a human patient, client device 102 may acquire image and/or video data of the patient and identification data that uniquely identifies the patient and transmit the image and/or video data and identification data to processing service 104.

In the example depicted in FIG. 1A, client device 102 includes a user interface 112 and a data acquisition component 114. User interface 112 allows for the exchange of information between a user and client device 102. For example, user interface 112 may include a display for displaying information to a user. User interface 112 may also include controls to allow a user to enter information to client device 102. The controls may be physical controls, such as buttons, switches, sliders, etc., or in the context of user interface 112 displaying a graphical user interface, the controls may be graphical user interface controls, such as buttons, dialog boxes, etc. User interface 112 may also include a touch screen for receiving user input. According to one embodiment, user interface 112 allows a user to acquire image and/or video data and identification data using client device 102, and to cause the acquired data to be transmitted to processing service 104, as described in more detail hereinafter.

Client device 102 includes a data acquisition component 114 for acquiring identification data that uniquely identifies object 116. The identification data may be any type of data that uniquely identifies object 116. Examples of identification data include, without limitation, an identification number, a serial number, an identification code (numeric or alphanumeric), a symbol, or other information. The identification data may be in human readable form, such as a numeric or alphanumeric string. Alternatively, the identification code may be in an encoded form, for example, in the form of a bar code, a QR code, a signature, or other encoded data. Data acquisition component 114 may also acquire image or video data of object 116.

Data acquisition component 114 may comprise hardware subcomponents, programmable subcomponents, or both. For example, data acquisition component 114 may include one or more cameras, scanners, memory units or other data storage units, buffers and code instructions for acquiring, storing and transmitting data, or any combination thereof. Data acquisition component 114 may be configured with a Wi-Fi interface and a barcode reader. The Wi-Fi interface may be used to transmit information to and from the data acquisition component 114. The barcode reader may be used to scan or otherwise acquire a code, such as a point of sale (POS) code displayed on an item. Client device 102 may be implemented by a wide variety of devices that may vary depending upon a particular implementation and the invention is not limited to client device 102 being implemented by any particular type of device. Examples of client device 102 include, without limitation, a camera, a smart phone, a tablet computer, a laptop computer, a personal digital assistant, a video recorder, or wearable computing devices such as smart watches, body or head cams, or eye glasses, such as Google Glass by Google, Inc., any of which configured with or without a scanner, such as a barcode scanner, a QR code scanner, etc., a scanner or other devices configured to acquire data and transmit the acquired data to other devices.

Client device 102 may include other components that may vary depending upon a particular implementation. According to one embodiment, client device 102 includes a location component that is capable of determining a current location of client device 102 and generating location data that indicates the current location of client device 102. One non-limiting example of a location component is a GPS module that can determine the current position of the client device 102 and generate data that indicates the GPS coordinates of that location. The GPS module may be internal or external to client device 102.

B. Processing Service

Processing service 104 receives image and/or video data and identification data ("acquired data") from client device 102 and integrates the acquired data into auto insurance system 106, EMR system 108 and other services 110. Processing service 104 may also process the acquired data as described in more detail hereinafter. Processing service 104 may include various hardware and software components that may vary depending upon a particular implementation and processing service 104 is not limited to any particular hardware and software components. In the example depicted in FIG. 1A, processing service 104 includes a data receiver 118, an integration service 120, a data transmitter 122, a user interface 124 and storage 126. Processing service 104 is not limited to the particular example depicted in FIG. 1A and may include fewer or additional elements depending upon a particular implementation.

Data receiver 118 is configured to receive data from client device 102 and may do so using various communication protocols and from various media. Example protocols include, without limitation, the File Transfer Protocol (FTP), the Telnet Protocol, the Transmission Control Protocol (TCP), the TCP/Internet Protocol (TCP/IP), the Hypertext Transfer Protocol (HTTP), the Simple Mail Transfer Protocol (SMTP), or any other data communications protocol. Data receiver 118 may be configured to read data from an FTP folder, an email folder, a Web server, a remote media such as a memory stick, or any other media.

For example, FIG. 1B depicts arrangement 100 as in FIG. 1A, except that in FIG. 1B, client device 102 includes an FTP client 130 and processing service 104 includes an FTP server 132. FTP server 132 is depicted in FIG. 1B as a separate element within processing service 104 for purposes of explanation only and FTP server 132 may be integrated into other elements within processing service 104, such as data receiver 118, depending upon a particular implementation. In this example, an FTP folder is created on storage 126 for storing acquired data received from client device 102. Client device 102 acquires image and/or video data and identification data and FTP client 1128 causes the acquired data to be transmitted to FTP server 132 on processing service 104 and stored in the FTP folder on storage 126. Data receiver 118 retrieves the acquired data from the FTP folder on storage 126 and transmits the retrieved data to integration service 120.

As another example, FIG. 1C depicts arrangement 100 as in FIG. 1A, except that in FIG. 1C, an email server 134 is provided and processing service 104 includes an email client 136. Email client 136 is depicted in FIG. 1C as a separate element within processing service 104 for purposes of explanation only and email client 136 may be integrated into other elements within processing service 104, such as data receiver 118. Client device 102 acquires image and/or video data and identification data and FTP client 1128 causes the acquired data to be transmitted to email server 134 via email. The acquired data may be embedded within an email or attached to the email as one or more attachments. Email client 136 retrieves the email from email server 134. Data receiver 118 obtains the email from email client 136, extracts or detaches the acquired data from the email and provides the acquired data to integration service 120. The data extraction/detachment may alternatively be performed by email client 136.

Figure 1D:
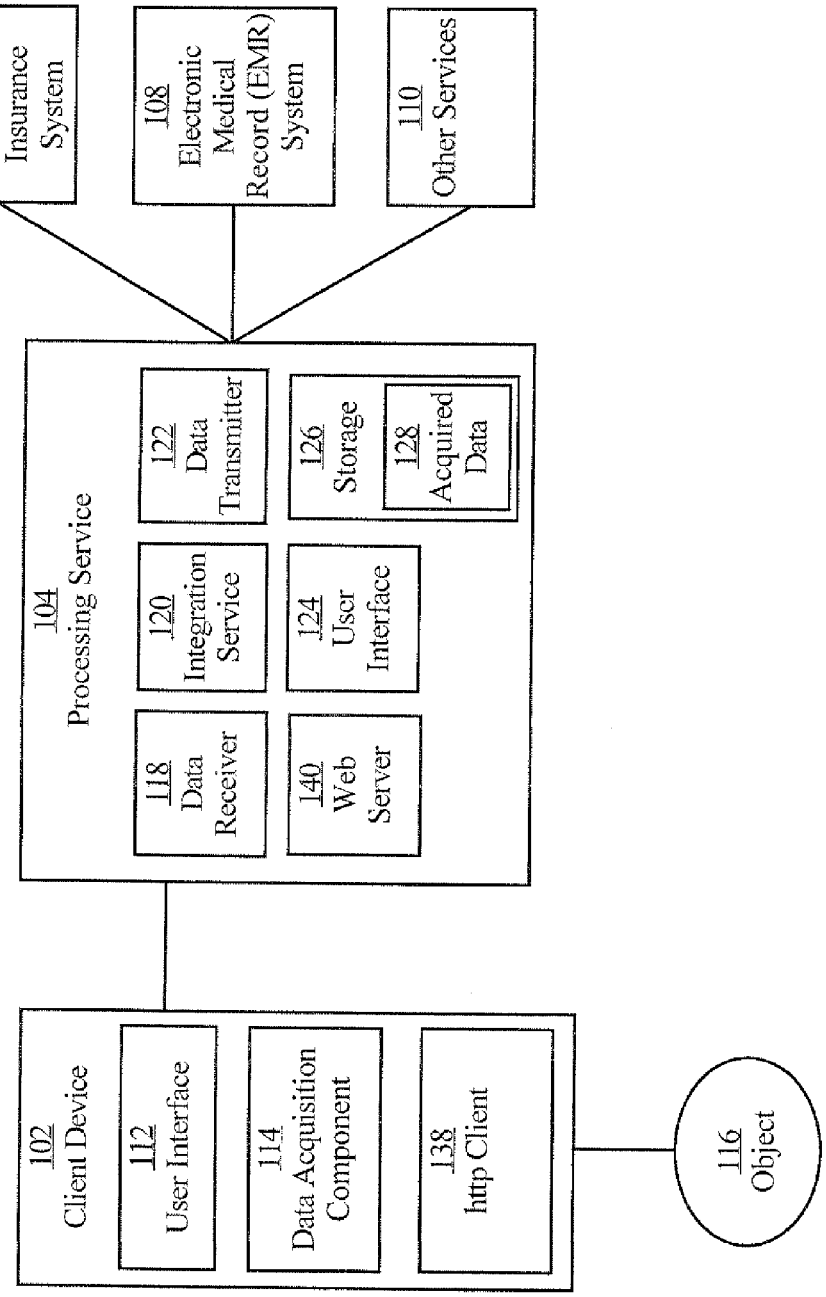

As another example, FIG. 1D depicts arrangement 100 as in FIG. 1A, except that in FIG. 1D, client device 102 includes an http client 138 and processing service 104 includes a Web server 140. In this example, client device 102 provides image or video data and identification data to processing service 104 by http client 138 issuing http POST commands to Web server 140. Data receiver 118 obtains the image and/or video data and identification data from Web server 140 and provides the data to integration service 120.

Integration service 120 is configured generally to receive data from data receiver 118, process the received data, and provide the data to data transmitter 122. As described in more detail hereinafter, this may include generating and/or updating record data stored in storage 126. Storage 126 may include any type of storage, such as volatile memory and/or non-volatile memory. Data transmitter 122 is configured to provide image and/or video data and identification data to auto insurance system 106, EMR system 108 and other services 110. Data transmitter 122 transmits the data to auto insurance system 106, EMR system 108 and other services 110 using standard techniques or alternatively, data transmitter 122 may transmit data to auto insurance system 106, EMR system 108 and other services 110 in accordance with Application Program Interfaces (APIs) supported by auto insurance system 106, EMR system 108 and other services 110.

User interface 124 provides a mechanism for a user, such as an administrator, to access processing service 104 and data stored on storage 126, as described in more detail hereinafter. User interface 124 may be implemented as an API for processing service 104. Alternatively, user interface 124 may be implemented by other mechanisms. For example, user interface 124 may be implemented as a Web server that serves Web pages to provide a user interface for processing service 104.

Figure 1E:
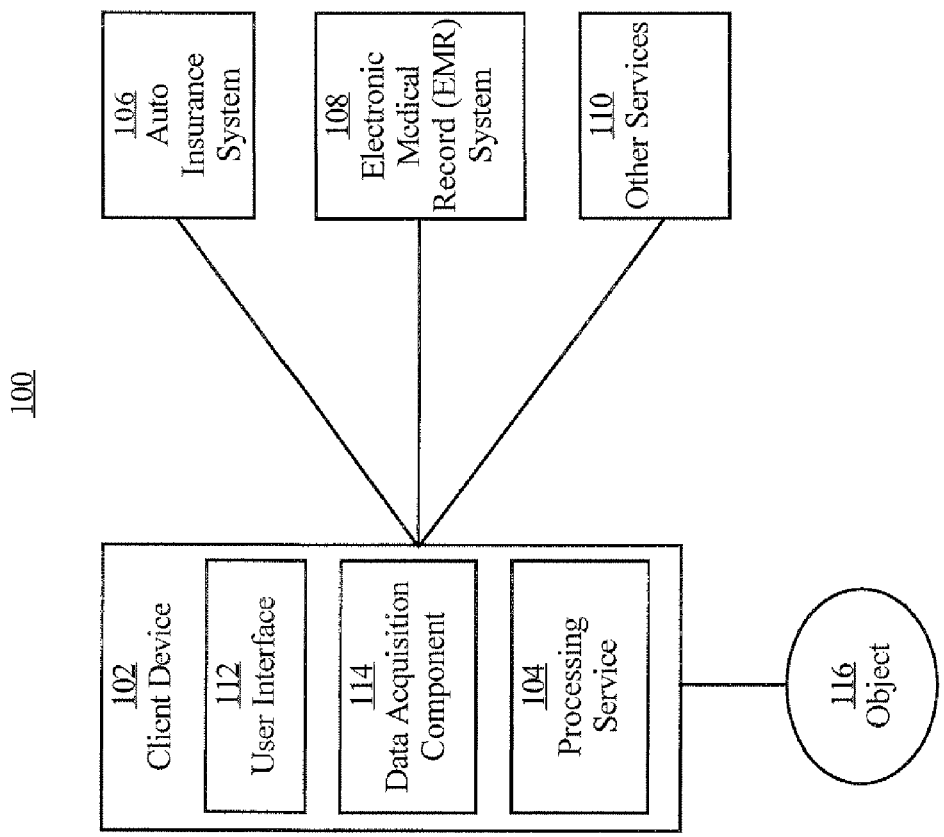

Processing service 104 may be implemented as a standalone process executing on a network element, such as a server or intermediary device. Processing service 104 may also be implemented on a client device, including client device 102, as depicted in FIG. 1E. In this example, processing service 104 is implemented on the client device 102 that is acquiring the image and/or video data and identification data.

III. Client Device Configuration and Data Acquisition

Figure 2:
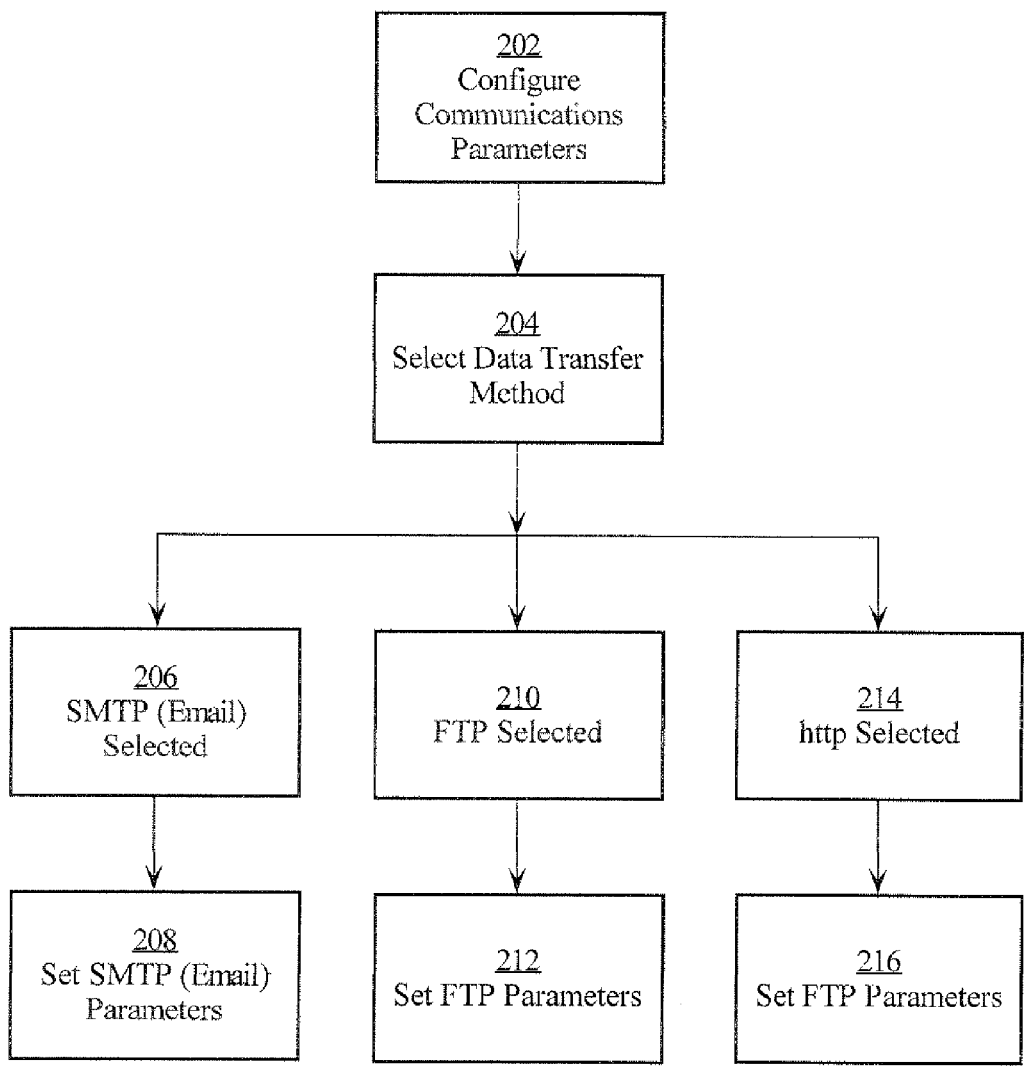
FIG. 2 is a flow diagram that depicts an approach for configuring a client device to transmit acquired data to a processing service.

Client device 102 is configured to transmit acquired data to processing service 104. The particular configuration required may vary depending upon the particular transmission mechanism used. FIG. 2 is a flow diagram 200 that depicts an approach for configuring client device 102 to transmit acquired data to processing service 104. In step 202, a user selects to configure communications parameters for client device 102. This may be accomplished, for example, by a user selecting a control on user interface 112 to access other controls for selecting communications parameters to be used by client device 102. As one example, a user may access a menu that offers a choice of SMPT (Email), FTP or http. In step 204, the user selects a particular data transfer method. In step 206, if SMTP (Email) is selected as the data transfer method, then in step 208, the user is provided access to set SMTP (Email) parameters. This may include, for example, an email address associated with processing service 104 to which emails with acquired data will be sent. In step 210, if FTP is selected as the data transfer method, then in step 212, the user is provided access to specify FTP parameters that may include, for example, an FTP server name, an FTP folder name and FTP credentials. In step 214, http is selected as the data transfer method, then in step 216, the user is provided access to specify http parameters, for example, a URL address to which acquired data may be posted. Although embodiments are described herein in the context of client device 102 being configured locally, i.e., via client device 102, client device 102 may also be configured remotely from another device. In this situation, a user of a remote device contacts client device 102 and accesses configuration options provided by a software application executing on client device 102. This may include authenticating a user prior to granting the user access to the software application for configuring client device 102. Client device 102 may be configured to support multiple data transfer methods.

Figure 3A:
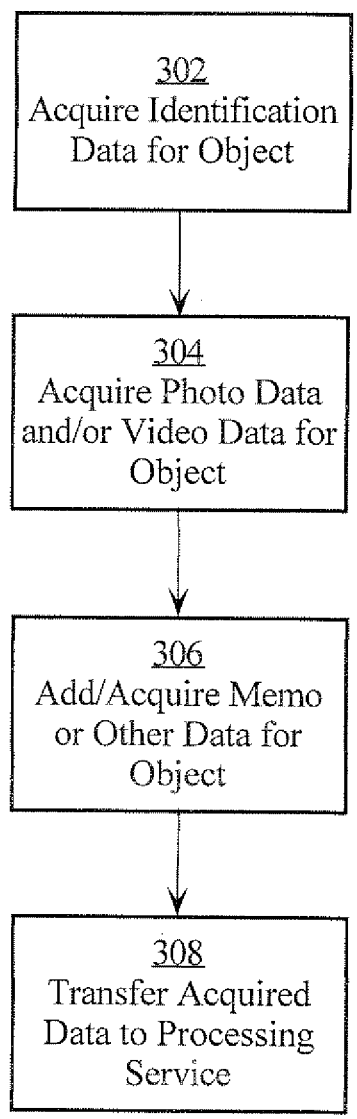
FIG. 3A is a flow diagram that depicts an approach for acquiring data with a client device and transferring the acquired data to a processing service.

Once client device 102 has been configured to transmit acquired data to processing service 104, data acquisition may be performed. FIG. 3A is a flow diagram 300 that depicts an approach for acquiring data with a client device and transferring the acquired data to a processing service. In step 302, identification data is acquired for an object. Referring to FIG. 1A, a user of client device 102 invokes the data acquisition component 114 of client device 102 to acquire identification data that uniquely identifies object 116. For example, a user may select a button or other control on client device 102, including a graphical user interface control, to cause client device 102 to scan identification data for object 116, such as a number, code, etc. The identification data may be encoded, for example, in the form of a barcode, QR code, signature, etc. For example, suppose that client device 102 is a camera, smartphone or tablet computer with a scanner. In the auto insurance context, a user, such as an insurance adjustor or automobile repairman, uses the scanner on the camera, smartphone or tablet computer to scan a vehicle identification number (VIN) of an automobile or a part of an automobile involved in an accident. As another example, in the EMR context, a user, such as a physician, nurse or medical administrative staff, uses the scanner on the camera, smartphone or tablet computer to scan a patient identification number, a physician identification number, or both a patient and physician identification numbers. The data acquisition component 114 may be configured to generate scan data that may be in a wide variety of formats that may vary depending upon a particular implementation. For example, the scan data may be in an image data format, such as JPEG, TIFF, RAW, GIF, BMP, PNG, or in PDF.

Figure 4B:
FIGS. 4A and 4B are example photos of an automobile that has been involved in an accident.
Figure 4D:
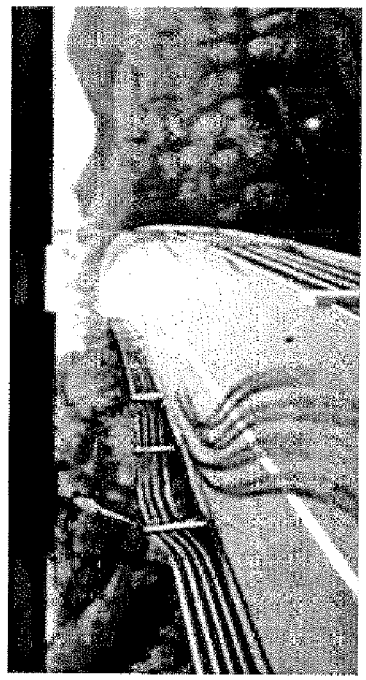
FIGS. 4C and 4D are example photos of a location of an automobile accident.
Figure 4A:
Figure 4C:
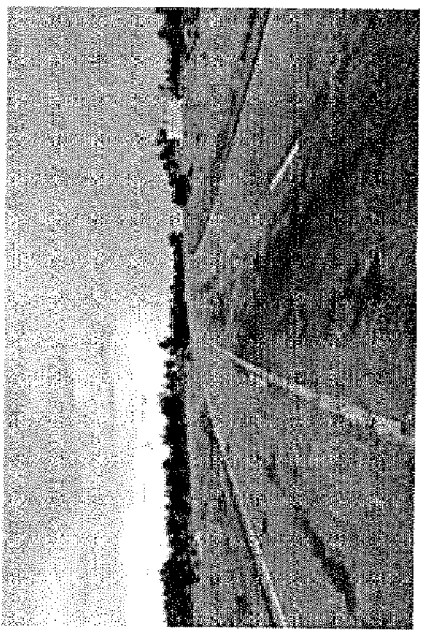

In step 304, photo data and/or video data is acquired for the subject object. Referring to FIG. 1A, a user causes client device 102 to acquire photo data and/or video data of object 116. This may include the user selecting one or more buttons or controls on client device 102 to activate a camera or video recorder on client device 102 to acquire the photo data and/or the video data of object 116. Referring again to the prior example where client device 102 is a camera, smartphone or tablet computer, in the auto insurance context, a user, such as an insurance adjustor or automobile repairman, uses the camera, smartphone or tablet computer to take photos or video of an automobile or a part of an automobile involved in an accident. FIGS. 4A and 4B are example photos of an automobile that has been involved in an accident. FIGS. 4C and 4D are example photos of a location of an automobile accident. As another example, in the EMR context, a user, such as a physician, nurse or medical administrative staff, uses the camera, smartphone or tablet computer to take photos or video of a patient. The image and/or video data may be in any of a wide variety of formats that may vary depending upon a particular implementation. Example image data formats include, without limitation, JPEG, TIFF, RAW, GIF, BMP, PNG, etc., and example video data formats include, without limitation, H.26X, M-PEG-X, etc.

In step 306, memorandum (memo) or other data for the object is acquired and/or added to supplement the acquired photo or video data. The memo or other data may include a wide variety of data that may vary depending upon a particular implementation. Memo or other data may be entered by a user via the user interface 112 of client device 102. For example, client device 102 may display a graphical user interface that allows a user to type alphanumeric characters into one or more text fields, or into a form. For example, in the auto insurance context, a user, such as an insurance adjustor or automobile repairman, may enter an insurance claim number, a vendor name, a part cost and point-of-sale or point-of-service (POS) barcode number for the part.

FIG. 5A depicts a table of example memo information that may be entered by a user for an automobile involved in an accident. As another example, in the EMR context, a user, such as a physician, nurse or medical administrative staff, may enter information associated with the patient, such as physician or staff notes about the patient, current medications, allergies, etc. FIG. 5B depicts a table of example memo information that may be entered by a user for a patient in the EMR context.

The information may also include annotation information for acquired image data and video data. For example, FIG. 6A depicts a graphical user interface of a client device in the form of a camera that displays a region on a patient's body. The camera includes a capability for a user, such as a physician, to annotate the picture to identify an area of interest, as depicted in FIG. 6B. This may be accomplished, for example, using user interface controls on the camera. Alternatively, the camera may be configured with a touch screen and the physician or other medical personnel may annotate the photo using a stylus or finger. The annotation information is represented by data that may be transmitted to the processing service 104 with the photo data.

An example of other data that may be acquired for the object is location data. For example, client device 102 may include a GPS component that is capable of determining the current location of client device 102 and generate data that indicates the GPS coordinates of the client device 102. This information may be helpful in a wide variety of contexts. For example, in the auto insurance context, the location information may be used to confirm the location of the accident and/or the automobile. The location information may also include a name of a location. For example, in the EMR context, a user may use client device 102 to scan a barcode or QR code of an examination room, emergency room, etc., to acquire information about the location where the image and/or video data was acquired. In this example, the barcode may specify the name of a medical facility and/or room or location within the medical facility. This information may be later used to verify the exact location where the image and/or video data was acquired. The other information may also include timestamp information that may be used to document when the image and/or video data were acquired. The other information may also include data that identifies a user of client device 102. The user data may be obtained when the user accesses client device 102 or when the user accesses an application on client device 102 for acquiring image and/or video data and identification data.

In step 308, client device 102 transfers the acquired data to processing service 104. This may include the image and/or video data, as well as the memo or other data acquired at client device 102. Client device 102 may transfer the data to processing service 104 using any of the techniques described herein, for example, via FTP, via email, or via http POST commands. The approach depicted in FIG. 3A may also include a user selecting an external service to which the acquired identification data, photo data, video data and memo and other data is to be transferred. In this situation, data identifying the selected external service is provided to processing service 104.

The particular user interface employed to support the acquisition of object identification, image data and video data and the transfer of that data to an external service may vary depending upon a particular implementation and embodiments are not limited to any particular implementation. FIG. 3B depicts an example graphical user interface 350 that allows a user to select image data and scan data acquired at the site of an automobile accident and transfer the selected image data and scan data to an auto insurance service. FIG. 3B is depicted and described in the context of selecting image data for purposes of explanation only and embodiments are not limited to image data per se and are applicable to other types of data, such as video data. The graphical user interface 350 for sending data to a service includes a set of controls 352 for selecting data and a set of controls 354 for selecting a service to receive the selected data.

In this example, a user, such as a law enforcement person or an insurance person, has used client device 102 to acquire scan data and image data for an automobile accident involving a first automobile and a second automobile. In this example, it is presumed that the user has the necessary credentials to use client device 102 in this manner and that the user has been properly authorized to access client device 102. The user has scanned the VIN number of a first automobile involved in the accident ("Scan 001"). The user has also taken three photos that include the first automobile ("Image 001"), the second automobile ("Image 002") and the accident location ("Image 003"). As indicated in FIG. 3B by the dashed boxes, the user has selected all three images and the scan data for transfer and has selected the service "Auto Insurance Service #2" to receive the data. The set of controls 352 also allows a user to add memo data and include location (loc) information with the acquired data. In the present example, the user has selected to add memo data and location information for the photo of the first automobile ("Image 001"). The memo information may be specified by the user via another graphical user interface screen that is not depicted in FIG. 3B. For example, in response to the user selecting the "Add Memo" box adjacent "Image 001", a dialog box may be displayed that allows the user to enter memo data for "Image 001". The location information may be provided by a location component of client device 102.

A set of user interface controls 356 allow the user to confirm the transfer to the selected service or cancel the transfer. Upon confirming the transfer, the acquired data, which in the present example includes the three images and the scanned VIN number of the first automobile, the memo data and the location data for "Image 001", are sent to processing service 104. User identification data that identifies a user of client device 102 may also be sent to processing service 104. The inclusion of data that indicates the selected external service, i.e., Auto Insurance Service #2, allows processing service 104 to route the image data and other data to Auto Insurance Service #2. The transferring of the VIN number of the first automobile with the images and other information allows the images and other information to be associated with data, for example an insurance claim record, maintained by the external service, i.e., Auto Insurance Service #2. In the example depicted in FIG. 3B, a user is given the capability to associate scan data with image data, but this is not required. For example, in some embodiments, the user interface 112 of client device 102 may prompt a user to first scan data that uniquely identifies object 116, such as an identification or serial number, bar code, QR code, etc., and then take one or more photos or videos of object 116. In this situation, the scanned data may be automatically associated with and transmitted to processing service 104 with the corresponding photos or videos.

There is no particular form or order in which the image or video data and identification data for object 116 are transmitted by client device 102 to processing service 104. For example, a user of client device 102 may use a camera of client device 102 to first acquire image or video data of object 116 and then use the data acquisition component 114 to acquire the identification data for object 116, for example, by scanning a bar code, QR code, etc., for object 116. The image or video data and identification data may be transmitted by client device 102 to processing service 104 separately or together, depending upon a particular implementation.

IV. Data Reception and Processing

Figure 7C:
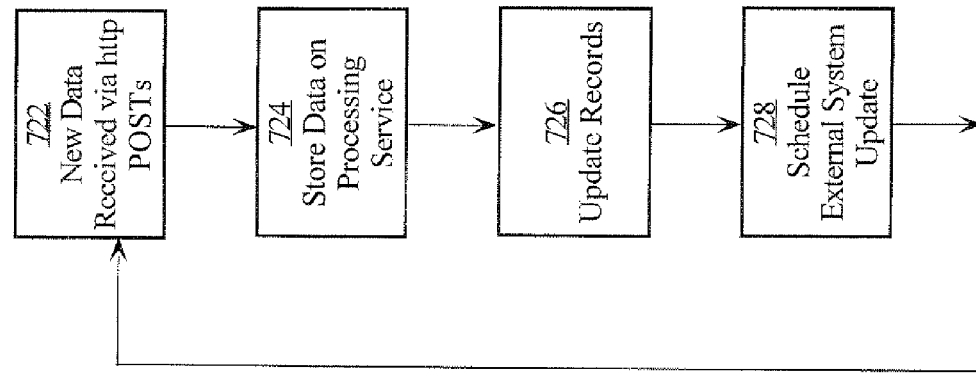
FIGS. 7A-7C are flow diagrams that depict example approaches for a processing service to receive acquired data from client device.
Figure 7B:
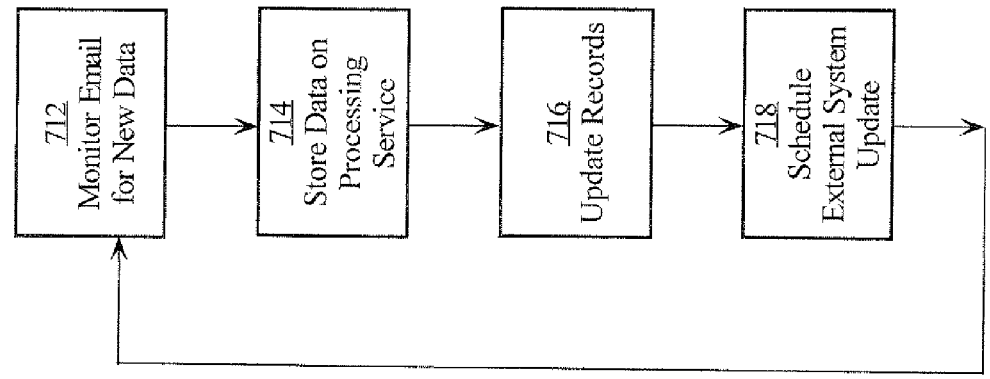
Figure 7A:
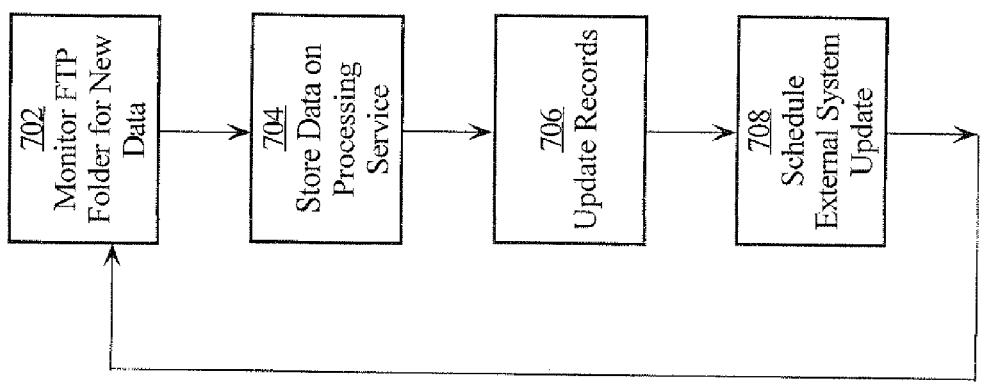

As previously described herein, client device 102 may transfer acquired data to processing service 104 using a wide variety of methods. FIGS. 7A-7C are flow diagrams that depict example approaches for processing service 104 to receive acquired data from client device 102. The flow diagram of FIG. 7A corresponds to processing service 104 receiving acquired data from client device 102 using FTP, as previously described herein with respect to FIG. 1B. In this approach, it is presumed that an FTP folder has been created on storage 126. The approach is described in the context of a single FTP folder for purposes of explanation only, and the approach is applicable to any number of FTP folders.

In step 702, processing service 104, or a component thereof, monitors the FTP folder to determine whether new data has been received from client device 102. The new data may include object identification data, image data, video data, other data, such as user identification, memo, location and timestamp data, as well as data that indicates a target external service.

In step 704, when new data is detected, then processing service 104 retrieves the new data from the FTP folder and in step 706 creates and/or updates record data. Various types of record data may be stored and maintained by processing service 104 and the format and content of record data maintained by processing service 104 may vary depending upon a particular implementation. Record data may be stored and managed on storage 126 as acquired data 128. Data stored on storage 126, including acquired data 128, may be stored in a secure manner, for example, using encryption. This may be helpful in situations where data stored on storage 126 includes sensitive information such as personal medical information or other information that might pertain to legal claims, such as automobile accident information. Data may be stored on storage 126 in a manner to comply with regulatory requirements. For example, regulatory requirements may specify a particular format and/or encryption that is to be used for certain types of data, such as medical information.

FIG. 8A depicts an example data structure implemented by processing service 104 in the auto insurance context. In this example, a user table includes, for each user, a user identification (ID), an authentication token, such as a password, and FTP folder for the user and an email address. The user table is associated with an insurance claim item that includes a user ID, a barcode, memo data, an ImageLink that provides a link to images for the insurance claim, a status and location data in the form of GPS data. In FIG. 8A, the user table is indexed by a primary key (PK) associated with a user. A value of the PK is indicated by an identifier (ID). The user table may store data for one or more users, and may therefore have one or more entries, each entry having a unique ID. The insurance claim item table may be indexed by a primary key (PK), which may correspond to the same PK in the user table.

FIG. 8B depicts an example data structure implemented by processing service 104 in the EMR context. In this example, a user table is the same as the user table depicted in FIG. 8A and includes, for each user, a user identification (ID), an authentication token, such as a password, and FTP folder for the user and an email address. The user table is associated with a patient image item that includes a user ID, a barcode, memo data, an ImageLink that provides a link to images for the insurance claim, a status and location data in the form of GPS data. The patient image item data structure may be indexed by a primary key (PK), which may correspond to the same PK in the user table of FIG. 8B.

In step 706, processing service 104 determines whether the data retrieved from the FTP folder is new data and if so, creates and stores on storage 126, a new record for the user. If the data retrieved from the FTP folder is for an existing record, for example additional photos for an insurance claim, then processing service 104 updates the existing record.

In step 708, processing service 104 schedules an external system update which, when processed, causes the data acquired by client device 102 to be provided to auto insurance system 106, EMR system 108 or other services 110, as described in more detail hereinafter. Scheduling an external system update may include a variety of steps that may vary depending upon a particular implementation. For example, scheduling an external system update may include generating and storing an entry in a processing queue, updating a flag, or otherwise notifying integration service 120. FIGS. 7B and 7C are flow diagrams that depict a process similar to the process depicted by the flow diagram of FIG. 7A, except in the context of transmitting data acquired by client device 102 via email or via http POST commands, respectively. In step 712 of FIG. 7B, processing service 104, or a component thereof, determines whether an email has been received that contains new data. This may include, for example, communicating with email client 136 to determine whether an email has been received that includes new data from client device 102. In step 722 of FIG. 7C, processing service 104, or a component thereof, determines whether new data has been received from client device 102 via an http POST. This may include, for example, determining whether an http POST command has been received at a specified URL, or by communicating with Web server 140 to determine whether an http POST command has been received. Steps 714-718 of FIG. 7B and steps 724-728 of FIG. 7C are similar to steps 704-708 of FIG. 7A.

V. Transferring Acquired Data to External Services

Figure 9:
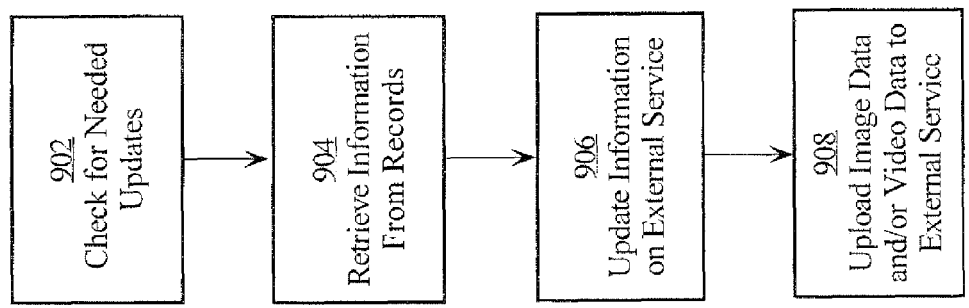
FIG. 9 is a flow diagram that depicts an approach for transferring acquired data to external services.

According to one embodiment, integration service 120 is configured to transmit acquired data to external services, such as auto insurance system 106, EMR system 108 and other services 110. FIG. 9 is a flow diagram 900 that depicts an approach for transferring acquired data to external services. In step 902, a check is made to determine where updates are needed. This may be performed using various approaches. For example, integration service 120 may determine whether a processing queue contains an entry that is waiting to be processed. As another example, integration service 120 may check for a flag or other type of notification that indicates that acquired data is ready to be transferred to an external service. Acquired data stored by processing service 104 may be prioritized for transfer to external services. A priority may be assigned to each set of acquired data received from a client device. A priority level may be specified by a user of a client device, for example, by specifying via user interface 112 that acquired data is high priority. Data indicating the priority is transferred from the client device to processing service 104 and stored with the acquired data so that acquired data stored at processing service 104 may be processed based upon the specified priorities. This may be useful in situations where it is helpful to process acquired data on an expedited basis. For example, a situation may exist where it is important to immediately process acquired data for a particular patient, or to process data for a particular auto accident.

Assuming that an update is needed, then in step 904, acquired data is retrieved from records. For example, integration service 120 may retrieve acquired data from records stored on storage 126. In step 906, information is updated on one or more external services. For example, integration service 120 may transfer to one or more of auto insurance system 106, EMR system 108 or other services 110, data contained in tables stored on storage 126. In step 908, image and/or video data is uploaded to the external services, such as auto insurance system 106, EMR system 108 or other services 110.

The updating and uploading performed in steps 906 and 908 may include formatting the acquired data to according to a data format supported by the external service to which the acquired data is being transmitted. For example, auto insurance system 106 may require that uploaded data be in a particular format or include specified fields in a particular order that may be different than EMR system 108. As another example, some external services may require that uploaded data be formatted in a secure manner. For example, EMR system 108 may require that uploaded data be encrypted using a particular encryption technique and/or a particular encryption key. The updating and uploading of acquired data may be performed in accordance with a particular API supported by the external services. For example, auto insurance system 106 may support a particular API that specifies commands for creating an auto insurance claim record on auto insurance system 106, updating the claim record with information and for uploading image and/or video data to auto insurance system 106. According to one embodiment, integration service 120 formats the data in accordance with a particular format and/or API required by an external service and invokes data transmitter 122 to cause the formatted data to be transmitted to the external service.

The approaches described herein are applicable to any number and types of client devices. Processing service 104 may receive acquired data from multiple client devices of different types, process the acquired data and integrated the acquired data into multiple external services, such as auto insurance system 106, EMR system 108 and other services 110. This may provide significant benefits in a wide variety of industries. For example, auto insurance companies may benefit from implementing processing service 104 within their information technology systems to allow their field agents, appraisers and third party repair services to take photos of automobiles involved in accidents and have those photos automatically integrated into the insurance claim processing systems of the auto insurance companies. As another example, medical insurance companies may benefit from implementing processing service 104 within their information technology systems to allow physicians and other medical personnel to take photos of patients and have those photos automatically integrated into the claims processing systems of the medical insurance companies. Alternatively, processing service 104 may be implemented as a third party service that is used by multiple auto and medical insurance companies.

VI. Processing Service Administration

According to one embodiment, processing service 104 is configured to provide an administrative user interface for performing various administrative functions. Example administrative functions include, without limitation, viewing and managing histories of the acquired data transferred to external services, viewing and managing error logs, managing user information and other functions. The administrative user interface may be implemented by user interface 124 in various forms that may vary depending upon a particular implementation. For example, the administrative user interface may be implemented by one or more APIs supported by user interface 124. As another example, the administrative user interface may be implemented as a Web interface. In this example, user interface 124 includes the capability to generate and transmit to a client device one or more Web pages that implement the administrative user interface.

Figure 10:
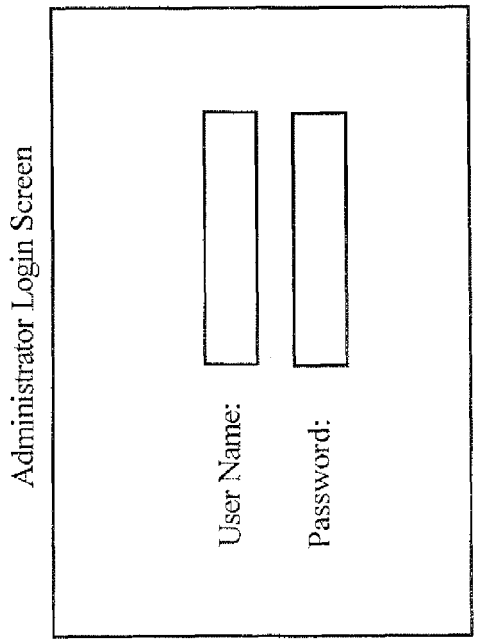
FIG. 10 depicts an example administrator login screen that may be implemented as a Web page.
Figure 11A:
FIGS. 11A and 11B depict example administrative user interface screens in the auto insurance context.
Figure 11B:

FIG. 10 depicts an example administrator login screen 1000 that may be implemented as a Web page by user interface 124. In this example, a user is queried to enter a user ID and password that are authenticated by processing service 104 prior to granting access to the administrative functions provided by processing service 104. FIGS. 11A and 11B depict example administrative user interface screens 1100, 1150 in the auto insurance context. In FIG. 11A, screen 1100 depicts a Web page that includes a menu of four options: Upload History, Error Log, User Information and Administration. In screen 1100, a user has selected the Upload History option and the Upload History is displayed. In this example, the upload history includes four entries, each entry corresponding to an upload of acquired data to auto insurance system 106. The acquired data for each upload includes a VIN number of a subject automobile, memo data, an upload time, location data in the form of GPS data and an image. Two of the data uploads pertain to insurance claim #14322 and the other two data uploads pertains to two other insurance claims. In this example, the VIN number, memo data, or both, may be used to associate the upload data with data stored in auto insurance system 106.

In screen 1150 of FIG. 11B, a user has selected the Error Log option and an error log is displayed that includes two entries. In this example, the error log indicates the data uploads for which an error occurred during the upload. For example, a network communication error or an error with auto insurance system 106 may have prevented acquired data from being successfully uploaded. The User Information option may allow an administrator to specify authorization information for users that are authorized to access processing service 104. This may include, for example, access constraints and data transfer constraints for users.

Figures 12A, 12B:
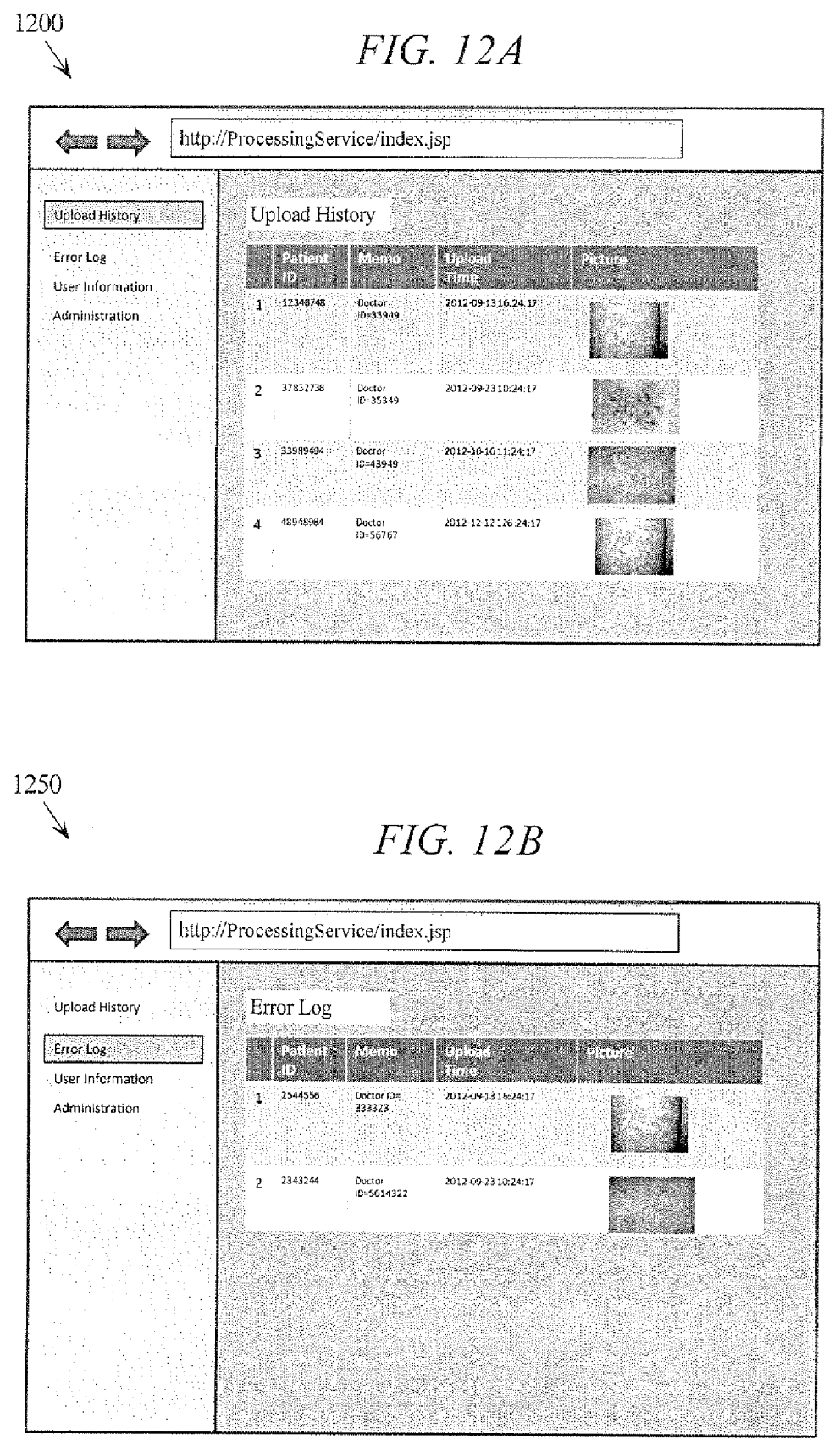

FIGS. 12A and 12B depict example administrative user interface screens 1200, 1250 in the EMR context. The particular examples depicted in FIGS. 11A, 11B, 12A and 12B are provided for explanation purposes only and embodiments are not limited to these examples. The particular user interfaces implemented by user interface 124 may vary depending upon a particular implementation.

VII. Implementation Mechanisms

Embodiments described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 13:
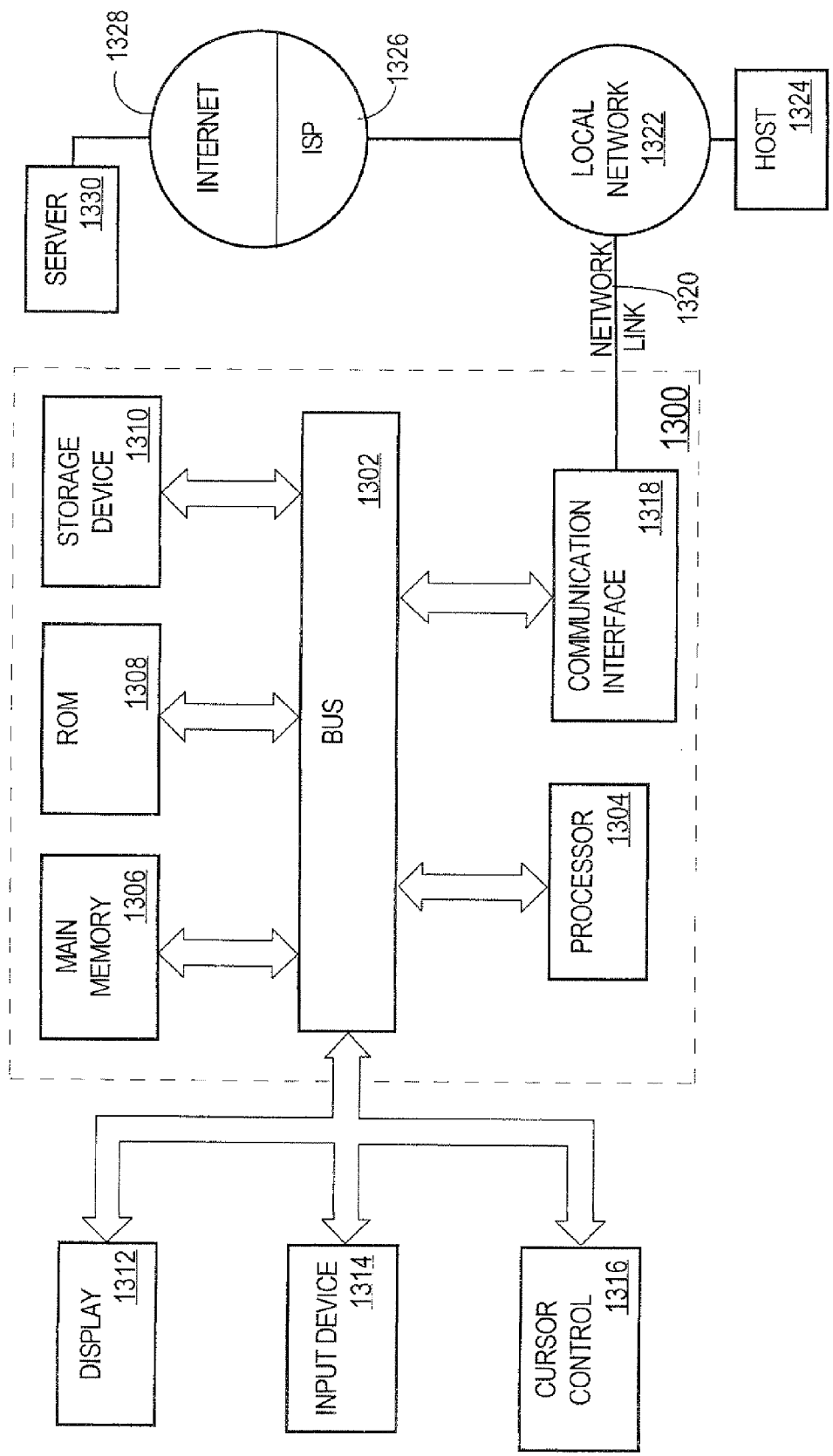
FIG. 13 is a block diagram that depicts an example computer system upon which embodiments may be implemented.

For example, FIG. 13 is a block diagram that illustrates a computer system 1300 upon which an embodiment of the invention may be implemented. Computer system 1300 includes a bus 1302 or other communication mechanism for communicating information, and a hardware processor 1304 coupled with bus 1302 for processing information. Hardware processor 1304 may be, for example, a general purpose microprocessor.

Computer system 1300 also includes a main memory 1306, such as a random access memory (RAM) or other dynamic storage device, coupled to bus 1302 for storing information and instructions to be executed by processor 1304. Main memory 1306 also may be used for storing temporary variables or other intermediate information during execution of instructions to be executed by processor 1304. Such instructions, when stored in non-transitory storage media accessible to processor 1304, render computer system 1300 into a special-purpose machine that is customized to perform the operations specified in the instructions.

Computer system 1300 further includes a read only memory (ROM) 1308 or other static storage device coupled to bus 1302 for storing static information and instructions for processor 1304. A storage device 1310, such as a magnetic disk or optical disk, is provided and coupled to bus 1302 for storing information and instructions.

Computer system 1300 may be coupled via bus 1302 to a display 1312, such as a cathode ray tube (CRT), for displaying information to a computer user. An input device 1314, including alphanumeric and other keys, is coupled to bus 1302 for communicating information and command selections to processor 1304. Another type of user input device is cursor control 1316, such as a mouse, a trackball, or cursor direction keys for communicating direction information and command selections to processor 1304 and for controlling cursor movement on display 1312. This input device typically has two degrees of freedom in two axes, a first axis (e.g., x) and a second axis (e.g., y), that allows the device to specify positions in a plane.

Computer system 1300 may implement the techniques described herein using customized hard-wired logic, one or more ASICs or FPGAs, firmware and/or program logic which in combination with the computer system causes or programs computer system 1300 to be a special-purpose machine. According to one embodiment, the techniques herein are performed by computer system 1300 in response to processor 1304 executing one or more sequences of one or more instructions contained in main memory 1306. Such instructions may be read into main memory 1306 from another storage medium, such as storage device 1310. Execution of the sequences of instructions contained in main memory 1306 causes processor 1304 to perform the process steps described herein. In alternative embodiments, hard-wired circuitry may be used in place of or in combination with software instructions to implement embodiments described herein. Thus, embodiments are not limited to any specific combination of hardware circuitry and software.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 1310. Volatile media includes dynamic memory, such as main memory 1306. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1302. Transmission media can also take the form of acoustic or light waves, such as those generated during radio-wave and infra-red data communications.

Various forms of media may be involved in carrying one or more sequences of one or more instructions to processor 1304 for execution. For example, the instructions may initially be carried on a magnetic disk or solid state drive of a remote computer. The remote computer can load the instructions into its dynamic memory and send the instructions over a telephone line using a modem. A modem local to computer system 1300 can receive the data on the telephone line and use an infra-red transmitter to convert the data to an infra-red signal. An infra-red detector can receive the data carried in the infra-red signal and appropriate circuitry can place the data on bus 1302. Bus 1302 carries the data to main memory 1306, from which processor 1304 retrieves and executes the instructions. The instructions received by main memory 1306 may optionally be stored on storage device 1310 either before or after execution by processor 1304.

Computer system 1300 also includes a communication interface 1318 coupled to bus 1302. Communication interface 1318 provides a two-way data communication coupling to a network link 1320 that is connected to a local network 1322. For example, communication interface 1318 may be an integrated services digital network (ISDN) card, cable modem, satellite modem, or a modem to provide a data communication connection to a corresponding type of telephone line. As another example, communication interface 1318 may be a local area network (LAN) card to provide a data communication connection to a compatible LAN. Wireless links may also be implemented. In any such implementation, communication interface 1318 sends and receives electrical, electromagnetic or optical signals that carry digital data streams representing various types of information.

Network link 1320 typically provides data communication through one or more networks to other data devices. For example, network link 1320 may provide a connection through local network 1322 to a host computer 1324 or to data equipment operated by an Internet Service Provider (ISP) 1326. ISP 1326 in turn provides data communication services through the world wide packet data communication network now commonly referred to as the "Internet" 1328. Local network 1322 and Internet 1328 both use electrical, electromagnetic or optical signals that carry digital data streams. The signals through the various networks and the signals on network link 1320 and through communication interface 1318, which carry the digital data to and from computer system 1300, are example forms of transmission media.

Computer system 1300 can send messages and receive data, including program code, through the network(s), network link 1320 and communication interface 1318. In the Internet example, a server 1330 might transmit a requested code for an application program through Internet 1328, ISP 1326, local network 1322 and communication interface 1318.

The received code may be executed by processor 1304 as it is received, and/or stored in storage device 1310, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. An apparatus comprising:
   one or more processors;
   one or more memories storing instructions which, when processed by the one or more processors, cause:
   receiving, via one or more wireless communications networks from a first mobile client device having at least a data acquisition component that includes a camera and is configured to acquire images of patients and identification data that uniquely identifies the patients, both first image data that includes a first set of images of a first patient and first identification data that uniquely identifies the first patient,
   generating and storing first record data that includes the first identification data and at least a reference to the first image data,
   receiving, via the or more wireless communications networks from a second mobile client device having at least a data acquisition component that includes a camera and is configured to acquire images of patients and identification data that uniquely identifies the patients, both second image data that includes a first set of images of a second patient and second identification data that uniquely identifies the second patient,
   generating and storing second record data that includes the second identification data and at least a reference to the second image data, and
   causing the first image data associated with the first patient, the first identification data that uniquely identifies the first patient, the second image data associated with the second patient and the second identification data that uniquely identifies the second patient to be transmitted via one or more communications networks to an electronic medical record system that is external to the apparatus utilizing one or more application program interfaces that are supported by the electronic medical record system and not supported by the first mobile client device and the second mobile client device.

2. The apparatus of claim 1, wherein the one or more memories store additional instructions which, when processed by the one or more processors, cause:
   receiving, via the one or more communications networks from the first mobile client device, additional first data that includes one or more of location data, text data, timestamp data, or user identification data, and
   storing the additional data in the first record data.

3. The apparatus of claim 1, wherein the one or more memories store additional instructions which, when processed by the one or more processors, cause:
   performing one or more of monitoring a file transfer protocol (FTP) folder, monitoring an electronic mail folder or receiving a hypertext transfer protocol (HTTP) post, and
   in response to detecting receipt of the first image data and the first identification data via the FTP folder, the electronic mail folder or the HTTP post, retrieving the first image data and the first identification data from the FTP folder, the electronic mail folder or the HTTP post.

4. The apparatus of claim 1, wherein the first identification data and the second identification data are encoded data represented by one or more of a bar code, a QR code, or a signature.

5. The apparatus of claim 1, wherein the data identification data that uniquely identifies the patients is acquired by the data acquisition components from the patients.

6. The apparatus of claim 1, wherein the first mobile client device includes a scanner for acquiring the first identification data in an encoded form and the second mobile client device includes a scanner for acquiring the second identification data in an encoded form.

7. The apparatus of claim 1, further comprising additional instructions which, when executed, cause the one or more processors to perform:

generating and providing via the one or more communications networks to the first mobile client device user interface data which, when processed at the first mobile client device, cause a graphical user interface to be displayed on the first mobile client device, wherein the graphical user interface allows a user to perform one or more of view and upload history for the electronic medical record system or view an error log for the electronic medical record system.

8. One or more non-transitory computer-readable media storing instructions which, when processed by one or more processors, cause:

receiving, via one or more wireless communications networks from a first mobile client device having at least a data acquisition component that includes a camera and is configured to acquire images of patients and identification data that uniquely identifies the patients, both first image data that includes a first set of images of a first patient and first identification data that uniquely identifies the first patient, generating and storing first record data that includes the first identification data and at least a reference to the first image data, receiving, via the or more wireless communications networks from a second mobile client device having at least a data acquisition component that includes a camera and is configured to acquire images of patients and identification data that uniquely identifies the patients, both second image data that includes a first set of images of a second patient and second identification data that uniquely identifies the second patient, generating and storing second record data that includes the second identification data and at least a reference to the second image data, and causing the first image data associated with the first patient, the first identification data that uniquely identifies the first patient, the second image data associated with the second patient and the second identification data that uniquely identifies the second patient to be transmitted via one or more communications networks to an electronic medical record system that is external to the apparatus utilizing one or more application program interfaces that are supported by the electronic medical record system and not supported by the first mobile client device and the second mobile client device.

9. The one or more non-transitory computer-readable media of claim 8, wherein the one or more memories store additional instructions which, when processed by the one or more processors, cause:

receiving, via the one or more communications networks from the first mobile client device, additional first data that includes one or more of location data, text data, timestamp data, or user identification data, and storing the additional data in the first record data.

10. The one or more non-transitory computer-readable media of claim 8, wherein the one or more memories store additional instructions which, when processed by the one or more processors, cause:

performing one or more of monitoring a file transfer protocol (FTP) folder, monitoring an electronic mail folder or receiving a hypertext transfer protocol (HTTP) post, and in response to detecting receipt of the first image data and the first identification data via the FTP folder, the electronic mail folder or the HTTP post, retrieving the first image data and the first identification data from the FTP folder, the electronic mail folder or the HTTP post.

11. The one or more non-transitory computer-readable media of claim 8, wherein the first identification data and the second identification data are encoded data represented by one or more of a bar code, a QR code, or a signature.

12. The one or more non-transitory computer-readable media of claim 8, wherein the data identification data that uniquely identifies the patients is acquired by the data acquisition components from the patients.

13. The one or more non-transitory computer-readable media of claim 8, wherein the first mobile client device includes a scanner for acquiring the first identification data in an encoded form and the second mobile client device includes a scanner for acquiring the second identification data in an encoded form.

14. The one or more non-transitory computer-readable media of claim 8, further comprising additional instructions which, when executed, cause the one or more processors to perform:

generating and providing via the one or more communications networks to the first mobile client device user interface data which, when processed at the first mobile client device, cause a graphical user interface to be displayed on the first mobile client device, wherein the graphical user interface allows a user to perform one or more of view and upload history for the electronic medical record system or view an error log for the electronic medical record system.

15. A computer-implemented method comprising:

receiving, via one or more wireless communications networks from a first mobile client device having at least a data acquisition component that includes a camera and is configured to acquire images of patients and identification data that uniquely identifies the patients, both first image data that includes a first set of images of a first patient and first identification data that uniquely identifies the first patient, generating and storing first record data that includes the first identification data and at least a reference to the first image data, receiving, via the or more wireless communications networks from a second mobile client device having at least a data acquisition component that includes a camera and is configured to acquire images of patients and identification data that uniquely identifies the patients, both second image data that includes a first set of images of a second patient and second identification data that uniquely identifies the second patient, generating and storing second record data that includes the second identification data and at least a reference to the second image data, and causing the first image data associated with the first patient, the first identification data that uniquely identifies the first patient, the second image data associated with the second patient and the second identification data that uniquely identifies the second patient to be transmitted via one or more communications networks to an electronic medical record system that is external to the apparatus utilizing one or more application program interfaces that are supported by the electronic medical record system and not supported by the first mobile client device and the second mobile client device.

16. The computer-implemented method of claim 15, wherein the one or more memories store additional instructions which, when processed by the one or more processors, cause:
receiving, via the one or more communications networks from the first mobile client device, additional first data that includes one or more of location data, text data, timestamp data, or user identification data, and
storing the additional data in the first record data.

17. The computer-implemented method of claim 15, wherein the one or more memories store additional instructions which, when processed by the one or more processors, cause:
performing one or more of monitoring a file transfer protocol (FTP) folder, monitoring an electronic mail folder or receiving a hypertext transfer protocol (HTTP) post, and
in response to detecting receipt of the first image data and the first identification data via the FTP folder, the electronic mail folder or the HTTP post, retrieving the first image data and the first identification data from the FTP folder, the electronic mail folder or the HTTP post.

18. The computer-implemented method of claim 15, wherein the first identification data and the second identification data are encoded data represented by one or more of a bar code, a QR code, or a signature.

19. The computer-implemented method of claim 15, wherein the data identification data that uniquely identifies the patients is acquired by the data acquisition components from the patients.

20. The computer-implemented method of claim 15, wherein the first mobile client device includes a scanner for acquiring the first identification data in an encoded form and the second mobile client device includes a scanner for acquiring the second identification data in an encoded form.

* * * * *